United States Patent [19]

Holmwood et al.

[11] Patent Number: 4,960,781
[45] Date of Patent: Oct. 2, 1990

[54] FUNGICIDAL DISAZOLYL-HYDROXYALKYL DERIVATIVES

[75] Inventors: Graham Holmwood, Wuppertal; Wolfgang Krämer, Burscheid; Erik Regel; Hans L. Elbe, both of Wuppertal; Karl H. Büchel, Burscheid; Stefan Dutzmann, Duesseldorf; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 481,780

[22] Filed: Feb. 16, 1990

Related U.S. Application Data

[63] Continuation of Ser. No. 244,232, Sep. 14, 1988, abandoned.

[30] Foreign Application Priority Data

Sep. 15, 1987 [DE] Fed. Rep. of Germany ....... 3730871

[51] Int. Cl.$^5$ ................. A01N 43/653; C07D 249/08
[52] U.S. Cl. .................... 514/383; 514/184; 514/373; 514/406; 548/101; 548/211; 548/266.2; 548/374
[58] Field of Search ...... 548/101, 211, 266.2, 548/374; 514/184, 373, 383, 406

[56] References Cited

U.S. PATENT DOCUMENTS

| | | | |
|---|---|---|---|
| 4,548,945 | 10/1985 | Holmwood et al. | 548/262 |
| 4,587,239 | 5/1986 | Regel et al. | 514/383 |
| 4,621,095 | 11/1986 | Regel et al. | 548/262 |
| 4,625,036 | 11/1986 | Boyle | 548/262 |
| 4,740,516 | 4/1988 | Regel et al. | 514/383 |

FOREIGN PATENT DOCUMENTS

| | | | |
|---|---|---|---|
| 0091398 | 10/1983 | European Pat. Off. | |
| 0105166 | 4/1984 | European Pat. Off. | |
| 131845 | 1/1985 | European Pat. Off. | 548/262 |
| 0180838 | 10/1986 | European Pat. Off. | |
| 0207590 | 1/1987 | European Pat. Off. | |

Primary Examiner—Glennon H. Hollrah
Assistant Examiner—Patricia L. Morris
Attorney, Agent, or Firm—Sprung, Horn, Kramer & Woods

[57] ABSTRACT

Fungicidal bisazolyl-hydroxyalkyl derivatives of the formula

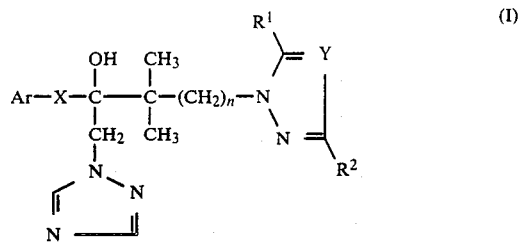

(I)

in which
Ar stands for optionally substituted aryl,
X stands for a grouping —CH$_2$CH$_2$—, —OCH$_2$—, —SCH$_2$— or —SH=CH—,
Y stands for a nitrogen atom or the grouping CR$^3$,
R$^1$, R$^2$ and R$^3$ stand for hydrogen, halogen or methyl, and
n stands for the numbers 0, 1 or 2, and acid addition salts and metal salt complexes thereof. Intermediates of the formulas

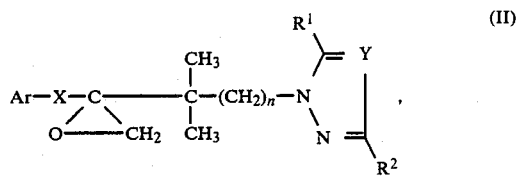

(II)

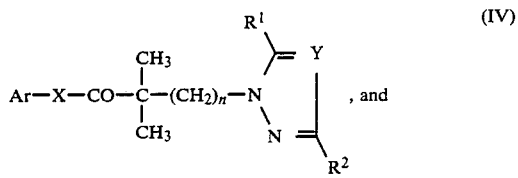

(IV)

, and

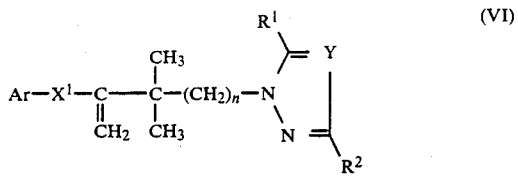

(VI)

are also new.

9 Claims, No Drawings

FUNGICIDAL DISAZOLYL-HYDROXYALKYL DERIVATIVES

This application is a continuation of application Ser. No. 244,232, filed Sept. 14, 1988, now abandoned.

The present invention relates to new bisazolyl-hydroxyalkyl derivatives, a process for their preparation, and their use as fungicides.

It has already been disclosed that numerous substituted triazolylalkyl-triazolylmethyl carbinols possess fungicidal properties (cf. EP-OS (European Patent Specification) No. 0,044,605 and EP-OS (European Patent Specification) No. 0,131,845). However, the action of these compounds is not always completely satisfactory, above all at low application rates and application concentrations.

New bisazolyl-hydroxyalkyl derivatives of the formula

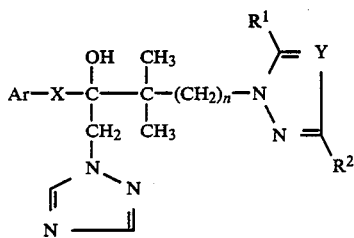

in which

Ar stands for optionally substituted aryl,

X stands for a grouping —$CH_2CH_2$—, —$OCH_2$—, —$SCH_2$— or —CH=CH—,

Y stands for a nitrogen atom or the grouping $CR^3$, $R^1$, $R^2$ and $R^3$ stand for hydrogen, halogen or methyl, and n stands for the numbers 0, 1 or 2, and acid addition salts and metal salt complexes thereof have now been found.

The new bisazolyl-hydroxyalkyl derivatives of the formula (I) have an asymmetrically substituted carbon atom and may therefore be obtained in the form of both optical isomers. The invention relates both to the racemates and to the individual isomers and mixtures thereof.

In addition, the compounds of the formula (I) according to the invention in which X stands for —CH=CH— can occur in the geometric isomer forms cis and trans. The invention relates both to the individual isomers and to mixtures thereof.

It has furthermore been found that bisazolyl-hydroxyalkyl derivatives of the formula (I) and their acid addition salts and metal salt complexes are obtained when oxiranes of the formula

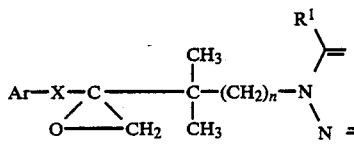

in which

Ar, X, Y, $R^1$, $R^2$ and n have the abovementioned meaning, are reacted with 1,2,4-triazole of the formula

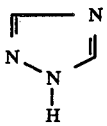

in the presence of a diluent and if appropriate in the presence of an acid-binding agent, and al$o if appropriate in the presence of a catalyst, and, if desired, the compounds of the formula (I) thus obtained are subjected to an addition reaction with an acid or a metal salt.

Finally, it has been found that the bisazolyl-hydroxyalkyl derivatives of the formula (I) and their acid addition salts and metal salt complexes are distinguished by very good fungicidal properties.

Surprisingly, the substances according to the invention possess a better fungicidal activity than substituted triazolylalkyl-triazolylmethyl carbinols known from the prior art which are constitutionally similar active compounds of the same type of action.

Formula (I) provides a general definition of the bisazolyl-hydroxyalkyl derivatives according to the invention. Preferred compounds are those of the formula (I) in which Ar stands for phenyl which is optionally monosubstituted, disubstituted or trisubstituted by identical or different substituents such as halogen, alkyl having 1 to 4 carbon atoms, alkoxy and alkylthio, each of which has 1 or 2 carbon atoms, nitro, halogenoalkyl, halogenoalkoxy and halogenoalkylthio, each of which has 1 or 2 carbon atoms and 1 to 5 identical or different halogen atoms, such as, preferably, fluorine atoms and chlorine atoms, alkoximinoalkyl having 1 to 4 carbon atoms in the alkoxy moiety and 1 or 2 carbon atoms in the alkyl moiety, and also phenyl, phenoxy, benzyl and benzyloxy, each of which is optionally substituted by halogen and/or alkyl having 1 or 2 carbon atoms;

Ar alternatively stands for naphthyl which is optionally monosubstituted, disubstituted or trisubstituted by identical or different substituents, substituents which may be mentioned being: halogen, alkyl and alkoxy, each having 1 or 2 carbon atoms, and also halogenoalkoxy having 1 or 2 carbon atoms and 1 to 5 identical or different halogen atoms, such as, preferably, fluorine atoms and chlorine atoms;

X stands for the groupings —$CH_2CH_2$—, —$OCH_2$—, —$SCH_2$— or —CH=CH—, where the hetero atom is bonded to the aryl radical if X stands for —$OCH_2$— or —$SCH_2$—; Y stands for a nitrogen atom or the grouping $CR^3$; $R^1$, $R^2$ and $R^3$ stand for hydrogen, chlorine, bromine or methyl, and n stands for the numbers 0, 1 or 2. Particularly preferred compounds are those of the formula (I) in which Ar stands for phenyl which is optionally monosubstituted, disubstituted or trisubstituted by identical or different substituents, substituents which may be mentioned being: fluorine, chlorine, bromine, iodine, methyl, methoxy, methylthio, nitro, trifluoromethyl, trifluoromethoxy, trifluoromethylthio, methoximinomethyl, methoximinoethyl, ethoximinomethyl, and phenyl, phenoxy, benzyl and benzyloxy, each of which is optionally substituted by fluorine, chlorine and/or methyl; or Ar stands for naphthyl;

X stands for the groupings —CH₂CH₂—, —OCH₂—, —SCH₂— or —CH=CH—, where the hetero atom is bonded to the aryl radical if X stands for —OCH₂— or —SCH₂—;

Y stands for a nitrogen atom or the grouping CR³;

R¹, R² and R³ stand for hydrogen, chlorine or methyl, and n stands for the numbers 0, 1 or 2.

In addition, preferred compounds according to the invention are addition products made from acids and the bisazolyl-hydroxyalkyl derivatives of the formula (I) in which Ar, X, Y, R¹, R² and n have the meanings which have already been mentioned in connection with the description of the substances according to the invention as being preferred for these substituents or this index.

The acids which may be added preferably include hydrohalogic acids such as, for example, hydrochloric acid and hydrobromic acid, in particular hydrochloric acid, furthermore phosphoric acid, nitric acid, monofunctional and bifunctional carboxylic acids and hydroxycarboxylic acids such as, for example, acetic acid, maleic acid, succinic acid, fumaric acid, tartaric acid, citric acid, salicylic acid, sorbic acid and lactic acid, and also sulphonic acids such as, for example, p-toluenesulphonic acid and 1,5-naphthalenedisulphonic acid.

Further preferred compounds according to the invention are addition products made from salts of metals of main groups II to IV and subgroups I and II and also IV to VIII of the periodic table of the elements, and the bisazolyl-hydroxyalkyl derivatives of the formula (I) in which Ar, X, Y, R¹, R² and n have the meanings which have already been mentioned in connection with the description of the substances according to the invention as being preferred for these substituents or for this index.

In this context, salts of copper, zinc, manganese, magnesium, zinc, iron and nickel are particularly preferred. Suitable anions of these salts are those which are derived from acids which lead to addition products tolerated by plants. Particularly preferred acids of this type are, in this connection, the hydrohaloic acids such as, for example, hydrochloric acid and hydrobromic acid, nitric acid and sulphuric acid.

If, for example 2-(4-chlorophenylethyl)-2-(pyrazol-1-yl-prop-2-yl)-oxirane and 1,2,4-triazole are used as starting substances, the course of the process according to the invention may be represented by the following equation:

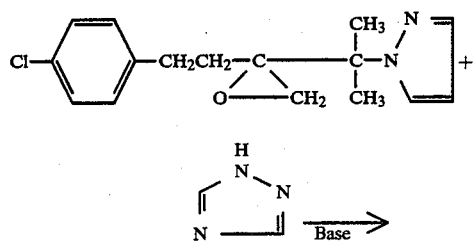

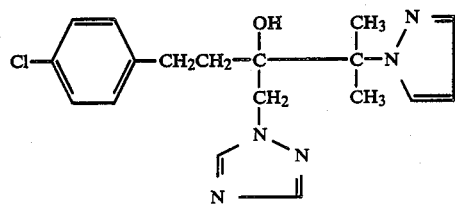

Formula (II) provides a general definition of the oxiranes to be employed as starting substances when carrying out the process according to the invention. In this formula, Ar, X, Y, R¹, R² and the index n preferably have the meanings which have already been mentioned in connection with the description of the substances of the formula (I) according to the invention as being preferred for these substituents or for the index.

The oxiranes of the formula (II) were hitherto unknown. They can be prepared by (a) in a first step, reacting ketones of the formula $$Ar-X^1-CO-\underset{\underset{CH_3}{|}}{\overset{\overset{CH_3}{|}}{C}}-(CH_2)_n-N\diagup\hspace{-0.3em}\underset{N}{\overset{\displaystyle\diagdown}{\phantom{x}}}\hspace{-0.9em}\diagdown_{R^2}^{\displaystyle Y} \qquad (IVa)$$

in which

Ar, Y, R¹, R² and n have the abovementioned meaning, and

X¹ stands for the groupings —CH₂CH₂—, —OCH₂— and —SCH₂—, with methyl-triphenyl-phosphonium bromide of the formula $$CH_3-\overset{\oplus}{P}\left[\phantom{x}\right]_3 Br^{\ominus} \qquad (V)$$

in the presence of a base and in the presence of a diluent, and then, in a second step, reacting the compounds of the formula $$Ar-X^1-\underset{\underset{CH_2}{||}}{\overset{\overset{CH_3}{|}}{C}}-\underset{\underset{CH_3}{|}}{\overset{\overset{R^1}{|}}{C}}-(CH_2)_n-N\diagup\hspace{-0.3em}\underset{N}{\overset{\displaystyle\diagdown}{\phantom{x}}}\hspace{-0.9em}\diagdown_{R^2}^{\displaystyle Y} \qquad (VI)$$

thus obtained in which

Ar, X¹, Y, R¹, R² and n have the abovementioned meaning, with peracid in the presence of a diluent; or (b) by reacting ketones of the formula $$Ar-X-CO-\underset{\underset{CH_3}{|}}{\overset{\overset{CH_3}{|}}{C}}-(CH_2)_n-N\diagup\hspace{-0.3em}\underset{N}{\overset{\displaystyle\diagdown}{\phantom{x}}}\hspace{-0.9em}\diagdown_{R^2}^{\displaystyle Y} \qquad (IV)$$

in which

Ar, X, Y, $R^1$, $R^2$ and n have the abovementioned meaning, either (α) with dimethyloxosulphonium methylide of the formula

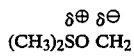

$$(CH_3)_2\overset{\delta\oplus}{S}O\ \overset{\delta\ominus}{C}H_2 \quad (VII)$$

or (β) with dimethylsulphonium methylide of the formula

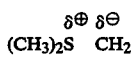

$$(CH_3)_2\overset{\delta\oplus}{S}\ \overset{\delta\ominus}{C}H_2 \quad (VIII)$$

in the presence of a diluent.

The ketones of the formula (IV) or (IVa) required as starting substances for the preparation of the oxiranes of the formula (II) were hitherto unknown. They can be prepared by processes known in principle (cf., for example, EP-OS (European Patent Specification) 0,084,834). Thus, ketones of the formula

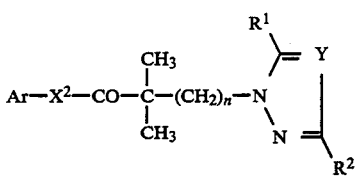

(IVb)

in which

Ar, Y, $R^1$, $R^2$ and n have the abovementioned meaning, and $X^2$ stands for the groupings —$OCH_2$— and —$SCH_2$—, are obtained by reacting halogenoketones of the formula

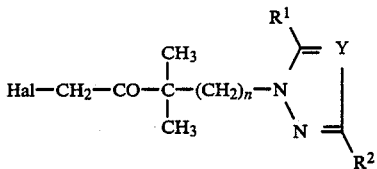

(IX)

in which

Y, $R^1$, $R^2$ and n have the abovementioned meaning, and Hal stands for chlorine or bromine, with compounds of the formula $$Ar—Z—H \quad (X)$$

in which

Ar has the abovementioned meaning and Z stands for oxygen or sulphur, in the presence of a base such as, for example, potassium carbonate or triethylamine, and in the presence of a diluent such as, for example, acetone or acetonitrile, at temperatures between 20° C. and 100° C.

Furthermore, ketones of the formula

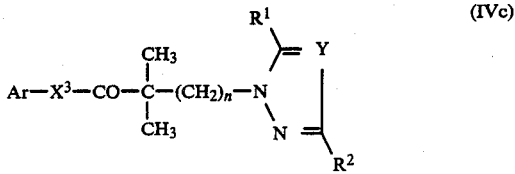

(IVc)

in which

Ar, Y, $R^1$, $R^2$ and n have the abovementioned meaning, and $X^3$ stands for the groupings —$CH_2CH_2$— and —$CH=CH$—, are obtained by reacting compounds of the formula

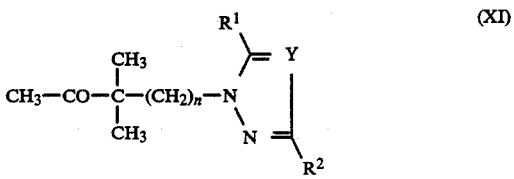

(XI)

in which

Y, $R^1$, $R^2$ and n have the abovementioned meaning, with aldehydes of the formula $$Ar—CHO \quad (XII)$$

in which

Ar has the abovementioned meaning, in the presence of a diluent such as, for example, ethanol, and in the presence of a base such as, for example, sodium hydroxide, at temperatures between 0° and 60° C., and if appropriate hydrogenating the resultant compounds of the formula

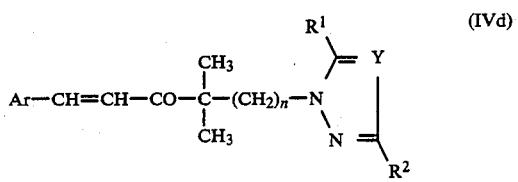

(IVd)

in which

Ar, $R^1$, $R^2$, Y and n have the abovementioned meaning, using hydrogen in the presence of a catalyst such as, for example, Raney nickel, in the presence of a diluent such as, for example, methanol, toluene or tetrahydrofuran, at temperatures between 40° and 180° C. (cf. also preparation examples).

In some cases, it is advantageous to also hydrogenate the keto group simultaneously with the —CH=CH— double bonding, and then to re-oxidize the former in a customary manner, such as, for example, using chromic acid/glacial acetic acid (cf. also preparation examples).

The halogenoketones of the formula (IX) are obtained in a known manner by customary halogenation of the compounds of the formula (XI).

The compounds of the formula (XI) are obtained in a known manner by reacting compounds of the formula

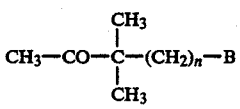

(XIII)

in which
B stands for a customary leaving group, such as chlorine, bromine, methylsulphonyloxy or p-methylphenylsulphonyloxy, and n has the abovementioned meaning, with azoles of the formula

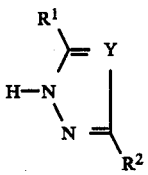

(XIV)

in which
Y, $R^1$ and $R^2$ have the abovementioned meaning, in the melt or if appropriate in the presence of a solvent such as, for example, acetone, and in the presence of an acid-binding agent such as, for example, potassium carbonate, at temperatures between 60° and 120° C. However, the azoles of the formula (XIV) may alternatively be employed in the form of their alkali metal salts, which are prepared in situ in a customary manner.

Both the compounds of the formula (X) and (XIII) and the aldehydes of the formula (XIII) and the azoles of the formula (XIV) are known or may be prepared by known processes.

Methyl-triphenyl-phosphonium bromide of the formula (V) furthermore required as a starting material for the preparation of the oxiranes of the formula (II) in process (a) is known.

The compounds of the formula (VI) required as starting substances in the second step of the preparation of the oxiranes of the formula (II) in the above process (a) were hitherto unknown.

The first step in process (a) for the preparation of the oxiranes of the formula (II) is carried out in the presence of a base. Suitable bases here are all bases which may normally be used for Wittig reactions of this type. Preferably, potassium tert.-butoxide is used.

Suitable diluents for carrying out the first step of the above process (a) for the preparation of the oxiranes of the formula (II) are all organic solvents customary for reactions of this type. Preferably, aromatic hydrocarbons such as benzene, toluene and xylene, may be used.

When carrying out the second step of the above process (a) for the preparation of the oxiranes of the formula (II), all the customary peracids are suitable as reagents for epoxidization. Meta-chloroperbenzoic acid and peracetic acid may preferably be used. Furthermore, it is also possible to employ a mixture of acetic acid and hydrogen peroxide.

Suitable diluents for carrying out the second step of the above process (a) for the preparation of the oxiranes of the formula (II) are all solvents customary for epoxidations of this type. Dichloromethane, chloroform, toluene, dichlorobenzene, acetic acid and other inert solvents may preferably be used.

When carrying out process (a) for the preparation of the oxiranes of the formula (II), the reaction temperatures may be varied within a certain range. In general, the first step is carried out at temperatures between 50° C. and 140° C., preferably between 80° C. and 120° C. The second step is generally carried out between 10° C. and 60° C., preferably between 20° C. and 50° C.

In general, process (a) for the preparation of the oxiranes of the formula (II) is carried out by employing 1 to 3 mols of methyl-triphenylphosphonium bromide of the formula (V) and 1 to 3 mols of base per mol of ketone of the formula (IVa) in the first step. In the second step, 1 to 2 mols of peracid are employed per mol of compound of the formula (VI) in each case. Working up is carried out in each case by customary methods.

The dimethyloxosulphonium methylide of the formula (VII) required as a reaction component in process (b) is known (cf. J. Amer. Chem. Soc. 87, 1363-1364 (1965)). In the above reaction, it is used in a freshly prepared state by producing it in situ by reacting trimethyloxo-sulphonium iodide with sodium hydride or sodium amide, in particular with potassium tert.-butoxide or sodium methoxide, in the presence of a diluent.

Dimethylsulphonium methylide of the formula (VIII) also suitable as a reaction component in process (b) is also known (cf. Heterocycles 8, 397 (1977)). In the above reaction, it is also employed in the freshly prepared state by preparing it in situ, for example from trimethylsulphonium halide or trimethylsulphonium methyl sulphate, in the presence of a strong base such as, for example, sodium hydride, sodium amide, sodium methoxide, potassium tert.-butoxide or potassium hydroxide, in the presence of a diluent, such as tert.-butanol or dimethyl sulphoxide.

Suitable diluents for carrying out process (b) are inert organic solvents. Alcohols, such as tert.-butanol, ethers, such as tetrahydrofuran or dioxane, furthermore aliphatic and aromatic hydrocarbons, such as benzene, toluene or xylene, and also strongly polar solvents, such as dimethyl sulphoxide, may preferably be used.

In process (b), the reaction temperatures may be varied within a relatively wide range. In general, the reaction is carried out at temperatures between 0° and 100° C., preferably between 10° and 60° C.

When carrying out process (b), 1 to 3 mols of dimethyloxosulphonium methylide of the formula (VII) or of dimethylsulphonium methylide of the formula (VIII) are preferably employed per mol of ketone of the formula (IV). Isolation of the oxiranes is carried out by customary methods.

The oxiranes of the formula (II) can be directly reacted further, if desired without isolation, in the process according to the invention.

Suitable diluents for the process according to the invention under the reaction conditions are inert organic solvents. Alcohols, such as ethanol, methoxyethanol or propanol; ketones, such as 2-butanone and N-methyl-pyrrolidone; nitriles, such as acetonitrile; esters, such as ethyl acetate; ethers, such as dioxane; aromatic hydrocarbons, such as benzene and toluene; or amides, such as dimethylformamide, may preferably be used.

Suitable bases for the process according to the invention are all inorganic and organic bases which are customarily usable. Alkali metal carbonates, such as sodium carbonate and potassium carbonate; alkali metal hydroxides, such as sodium hydroxide; alkali metal alkoxides, such as sodium methoxide, potassium methoxide, sodium ethoxide and potassium ethoxide; alkali metal hydrides, such as sodium hydride; and also tertiary lower alkylamines, cycloalkylamines and aralkylamines, such as in particular triethylamine, may preferably be u$ed.

Suitable catalysts for carrying out the process according to the invention are all reaction accelerators which may customarily be used for reactions of this type. α,α'-Azoisobutyronitrile may preferably be used.

When carrying out the process according to the invention, the reaction temperatures may be varied within a relatively wide range. In general, the process is carried out at temperatures between 0° and 200° C., preferably between 60° and 150° C.

The process according to the invention is normally carried out under atmospheric pressure. However, it is al$o possible to carry out the process under increased or reduced pressure.

Whén carrying out the process according to the invention, 1 to 2 mols of 1,2,4-triazole and, if appropriate, 1 to 2 mols of acid-binding agent are preferably employed per mol of oxirane of the formula (II). Working up and isolation of the final products are carried out by customary methods.

The compounds of the formula (I) obtainable in the process according to the invention can be converted into acid addition salts or metal salt complexes.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary methods of salt formation, for example by dissolving a compound of the formula (I) in a suitable inert solvent and adding the acid, for example hydrochloric acid, and can be isolated in a known manner, for example by filtering off, and purified, if necessary, by washing with an inert organic solvent.

Suitable salts for the preparation of metal salt complexes of the compounds of the general formula (I) are preferably those metal salts which have already been described further above.

The metal salt complexes of compounds of the formula (I) can be obtained in a simple manner by customary methods, for example by dissolving the metal salt in alcohol, for example ethanol, and adding the solution to compounds of the formula (I). Metal salt complexes can be isolated in a known manner, for example by filtering off, and purified, if necessary, by recrystallization.

The active compounds according to the invention exhibit a strong microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae;* Pseudomonas species, such as *Pseudomonas lachrymans;* Erwinia species, such as *Erwinia amylovora;* Pythium species, such as *Pythium ultimum;* Phytophthora species, such as *Phytophthora infestans;* Pseudoperonospora species, such as *Pseudoperonospora humuli* or *Pseudoperonospora cubense;* Plasmopara species, such as *Plasmopara viticola;* Peronospora species, such as *Peronospora pisi* or *P. brassicae;* Erysiphe species, such as *Erysiphe graminis;* Sphaerotheca species, such as *Sphaerotheca fuliginea;* Podosphaera species, such as *Podosphaera leucotricha;* Venturia species, such as *Venturia inaequalis;* Pyrenophora species, such as *Pyrenophora teres* or *P. graminea;* (conidia form: Drechslera, syn: Helminthosporium); Cochliobolus species, such as *Cochliobolus sativus;* (conidia form: Drechslera, syn: Helminthosporium); Uromyces species, such as *Uromyces appendiculatus;* Puccinia species, such as *Puccinia recondita;* Tilletia species, such as *Tilletia caries;* Ustilago species, such as *Ustilago nuda* or *Ustilago avenae;* Pellicularia species, such as *Pellicularia sasakii;* Pyricularia species, such as *Pyricularia oryzae;* Fusarium species, such as *Fusarium culmorum;* Botrytis species, such as *Botrytis cinerea;* Septoria species, such as Septoria nodorum; Leptosphaeria species, such as *Leptosphaeria nodorum;* Cercospora species, such as *Cercospora canescens;* Alternaria species, such as *Alternaria brassicae* and Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As plant-protecting agents, the substances according to the invention can be employed with particularly good success for combating Venturia (apple), Sphaerotheca (cucumber), as well as Erysiphe, Leptosphaeria, Cochliobolus, Pyrenophora, Pseudocercosporella and Cercospora in cereals, Pyricularia in rice, and also rusts, in particular in cereals. In addition, the compounds according to the invention possess a good broad range of action in vitro.

At suitable application rates, the substances according to the invention also shows a plant growth regulating action.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

When the compounds according to the invention are used as fungicides, the application rate can be varied within a substantial range, depending on the method of application. In the treatment of parts of plants, the active compound concentrations in the use forms are thus, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02%, are required at the place of action.

Preparation and use of the substances according to the invention can be seen from the following examples.

PREPARATION EXAMPLES

Example 1

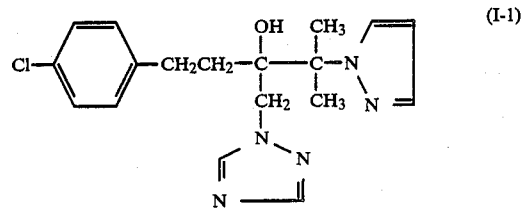

11 g (0.16 mol) of 1,2,4-triazole and 0.9 g (0.016 mol) of pulverulent potassium hydroxide are added to a solution of 26 g (0.08 mol) of 2-(4-chlorophenylethyl) -2-(pyrazol-1-yl-prop-2-yl)-oxirane in 150 ml of n-butanol. The mixture is stirred at 120° C. for 10 hours. The solvent is then removed by distillation under reduced pressure. The residue remaining is taken up in 200 ml of methylene chloride, and the organic phase is washed three times with 150 ml of water each time, dried over sodium sulphate and subsequently concentrated under reduced pressure. 24 g of an oily substance are obtained and purified by column chromatography using methylene chloride on silica gel 60 Merck. After recrystallization of the isolated product, 4.6 g (16% of theory) of 5-(4-chlorophenyl) -2-methyl-2-(pyrazol-1-yl)-3-(1,2,4-triazol-methyl) -pentan-3-ol of melting point 118° C. are obtained.

A further 5 g can be obtained from the mother liquor remaining from the recrystallization by repeated column chromatography.

Preparation of starting materials

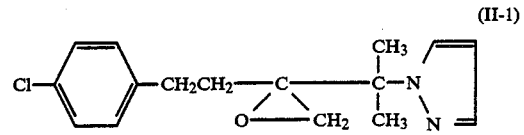

(Variant b)

17.6 g (0.08 mol) of trimethylsulphonium iodide are suspended in 50 ml of dimethyl sulphoxide. 9 g (0.08 mol) of potassium tert-butoxide are added to the mixture in portions in the course of 30 minutes and with stirring at room temperature. The mixture is then stirred for a further hour at room temperature. A solution of 22.1 g (0.08 mol) of 5-(4-chlorophenyl)-2-methyl-2-(pyrazol-1-yl)-pentan-3-one in 20 ml of dimethyl sulphoxide is subsequently added dropwise in the course of an hour at 5° C. The mixture is stirred for 22 hours at room temperature and then stirred into 1,000 ml of water. The mixture is extracted three times with 150 ml of methylene chloride, the organic phase is dried, and the solvent is removed by distillation in a water pump vacuum. The oxirane obtained is employed without further purification.

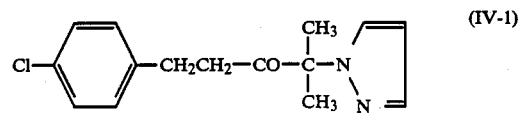

A solution of 6.4 g (0.064 mol) of chromic acid in 5 ml of water and 20 ml of glacial acetic acid is added dropwise at 5° C. to a solution of 23.5 g (0.085 mol) of 5-(4-chlorophenyl)-2-methyl-2-(pyrazol-1-yl) -pentan-3-ol in 60 ml of glacial acetic acid in the course of one hour. The mixture is subsequently stirred for a further 25 hours at room temperature. The mixture is stirred into 2,000 ml of water and extracted five times with 200 ml of methylene chloride each time, and the solvent is removed by distillation. 22.1 g (94% of theory) of 5-(4-chloro-phenyl)-2-methyl-2-(pyrazol-1-yl)-pentan-3-one of diffraction index $n^{23}_D = 1.5278$ are obtained.

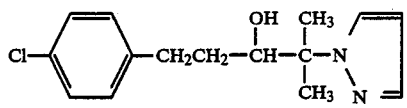

7 g of Raney nickel are added to a solution of 27.4 g (0.1 mol) of 5-(4-chlorophenyl)-2-methyl-2-(pyrazol -1-yl)-pent-3-on-4-ene in 200 ml of methanol, and the mixture is hydrogenated at 60° C. for 4 hours using hydrogen under a pressure of 40 to 50 bar. After the catalyst has been removed by suction and the methanol has been removed by distillation, 27.2 g of 5-(4-chlorophenyl)-2-methyl-2-(pyrazol-1-yl)-pentan-3-ol of refractive index $n^{20}_D = 1.5438$ are obtained.

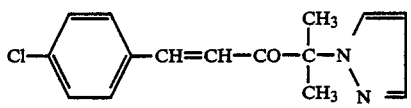

(IV-2)

44 ml of water and a solution of 64 g (0.45 mol) of p-chlorobenzaldehyde in 50 ml of ethanol are added to a solution of 69.5 g (0.45 mol) of 2-methyl-2-(pyrazol1-yl)-butan-3-one in 200 ml of ethanol. A solution of 1.35 g of sodium hydroxide in 13.5 ml of water is then added dropwise. The reaction is exothermic to 30° C. After the reaction mixture has been stirred for a further hour, a solution of 0.44 g (0.011 mol) of sodium hydroxide in 4.4 ml of water is added dropwise. The reaction mixture is allowed to stand for three days at room temperature, the solvent is removed by distillation, and the residue is taken up in 400 ml of methylene chloride. The organic phase is washed three times with 300 ml of water and 10 ml of glacial acetic acid each time. The organic phase is evaporated under reduced pressure, and the residue remaining is recrystallized from petroleum ether. 91.6 g (74.2% of theory) of 5-(4-chlorophenyl)-2-methyl-(pyrazol -1-yl)-pent-3-on-4-ene of melting point 60° C. are obtained.

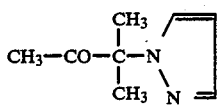

(XI-1)

1 mol of methyl bromoisopropyl ketone is added dropwise at 100° C. to a melt of 4 mols of pyrazole. The reaction mixture is stirred for a further hour. Following customary working up, 2-methyl-2-(pyrazol-1-yl)-butan-3one is obtained in a yield of 70%.

Example 2

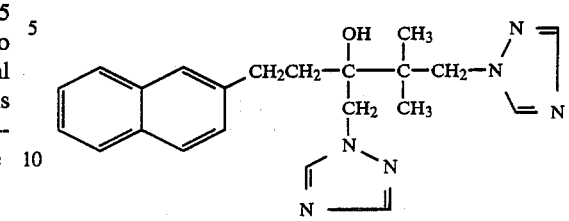

(I-2)

A solution of 10 g (0.031 mol) of 2-[1,1-dimethyl2-(1,2,4-triazol-1-yl)]-ethyl-2-(naphth-2-yl-ethyl)oxirane, 2.4 g (0.0348 mol) of 1,2,4-triazole, 0.4 g of sodium hydroxide, 0.1 g of water and a spatula tip of $\alpha,\alpha'$-azoisobutyronitrile in 100 ml of dimethylformamide is stirred at 100° C. for 5 hours, then cooled and evaporated under reduced pressure. The residue is dissolved in dichloromethane. The solution formed is washed three times with water, dried over sodium sulphate, and concentrated under reduced pressure. The residue is purified by column chromatography (silica gel/ethyl acetate and subsequently ethyl acetate/methanol = 1:1). 6.0 g (49.6% of theory) of 4,4-dimethyl-1-(2-naphthyl)-5-(1,2,4-triazol-1-yl)-3-(1,2,4-triazol-1-yl-methyl)-3-pentanol of melting point 77-80° C. are obtained.

Preparation of starting products

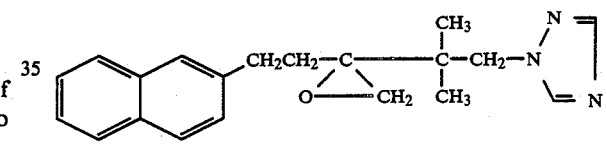

(II-2)

(Variant a)

A solution of 22 g (0.0721 mol) of 2-[1,1-di-methyl-2-(1,2,4-triazol-1-yl)]-ethyl-4-(2-naphthyl) -1-butene in 50 ml of dichloromethane is refluxed. In the course of 1.5 hours, a solution of 27.9 g (0.129 mol) of 80% strength m-chloroperbenzoic acid in 270 ml of dichloromethane is added dropwise. The mixture is subsequently refluxed for a further 4 hours, then cooled, and washed three times with 1-normal sodium hydroxide solution and twice with water. The organic phase is dried over sodium sulphate and concentrated under reduced pressure. 19.0 g (82.1% of theory) of 2-[1,1- dimethyl -2-(1,2,4-triazol-1-yl)]-ethyl-2-(naphth-2-yl-ethyl)-oxirane are obtained in the form of an oil.

$^1$H-NMR (in CDCL$_3$: 300 MHz) $\delta = 2.60$ (1H, d) and 2.73 (1H, d) for the epoxymethylene group.

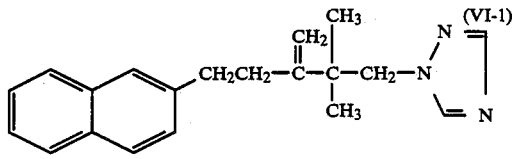

(VI-1)

A suspension of 57.3 g (0.16 mol) of methyltriphenylphosphonium bromide and 18.4 g (0.16 mol) of potassium tert-butoxide in 250 ml of absolute toluene is warmed to 90° C. under dry nitrogen. In the course of 30 minutes, a solution of 36.8 g (0.12 mol) of 4,4-dimethyl-1-(2-naphthyl) -5-(1,2,4-triazol-1-yl)-3-pentanone in 200 ml of absolute toluene is added dropwise. The reaction mixture is then stirred for 2 hours at 90° C., cooled, washed twice with water, and evaporated under reduced pressure. The residue is taken up in ethyl acetate the solution is cooled to 5° C. and the crystal slurry formed (triphenylphosphonium oxide) is filtered. The filtrate is concentrated under reduced pressure, and the residue is purified by column chromatography (silica gel; dichloromethane/acetic acetate=9:1).

27.0 g (73.8% of theory) of 2-[1,1-dimethyl-2-(1,2,4-triazol -1-yl)]-ethyl-4-(2-naphthyl)-1-butene are obtained in the form of an oily product.

$^1$H-NMR (300 MHz CDCL$_3$): δ=4.91 (1H, s) and 5.05 (1H, s) for the olefinic methylene group.

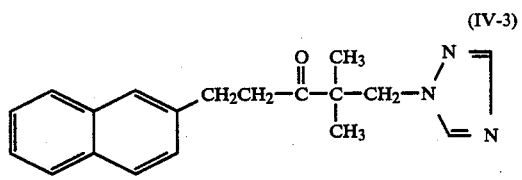
(IV-3)

15 g of Raney nickel are added to a solution of 67 g (0.22 mol) of 4,4-dimethyl-1-(2-naphthyl)-5-(1,2,4-triazol-1-yl)-1-penten -3-one in 400 ml of methanol, and the mixture is stirred in an autoclave at 90° C. for 4 hours under 90 bar of hydrogen. After the reaction mixture has been filtered and evaporated under reduced pressure, 55 g (81.4% of theory) of 4,4-dimethyl-1-(2-naphthyl) -5-(1,2,4-triazol-1-yl)-3-pentanone are obtained as a yellow solid of melting point 134° C.

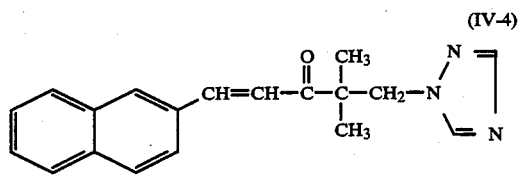
(IV-4)

59.3 g (0.38 mol) of 2-naphthaldehyde and 63.5 g (0.38 mol) of 3,3-dimethyl-4-(1,2,4-triazol-1-yl)-2-butanone are dissolved in 200 ml of ethanol, and a solution of 1.5 g of sodium hydroxide in 15 ml of water is added. The mixture is stirred for 1 hour at room temperature, 0.5 g of solid sodium hydroxide is added, the mixture is stirred for a further hour, 50 ml of water are added, and the mixture is stirred for a further 16 hours. 100 ml of water are then added to the reaction mixture. The precipitate is filtered off by suction and dissolved in dichloromethane. The solution is washed twice with water, dried over sodium sulphate and evaporated under reduced pressure.

115 g (99% of theory) of 4,4-dimethyl-1-(2-naphthyl) -5-(1,2,4-triazol-1-yl)-1-penten-3-one are obtained as a white solid of melting point 103°–104° C.

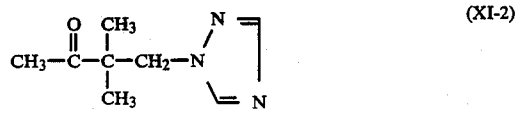
(XI-2)

In the course of 3 hours, 60 g (2 mols of sodium hydride (80% strength in paraffin oil) are added to a solution of 138 g (2 mols) of 1,2,4-triazole in 1,600 ml of absolute dimethylformamide, with vigorous evolution hydrogen. The mixture is stirred for a further 30 minutes at room temperature. 388 g (2 mols) of 3,3-dimethyl -4-[(methylsulphonyl)oxy]-2-butanone are then added dropwise in the course of 15 minutes. The reaction mixture is then stirred for 16 hours at 95° C. 100 ml of water are firstly added carefully to the reaction mixture, and the mixture is then poured into 4 l of water. The mixture is extracted six times with dichloromethane. The combined organic phases are washed once with plenty of water, dried over sodium sulphate and concentrated under a high vacuum. After column chromatography (silica gel; dichloromethane/ethyl acetate=1:1), 290 g (86.8% of 3,3-dimethyl -4-(1,2,4-triazol-1-yl)-2-butanone are obtained as an oil with a content of 97% after GC.

$^1$H-NMR (300 MHz CDCL$_3$): δ=1.23 (6H, s; C(CH$_3$)$_2$), 2.19 (3H, s; CH$_3$CO), 4.32 (2H, s; CH$_2$-triazole), 7.90 (1H, s) and 8.12 (1H, s) for the triazole ring protons.

In accordance with the Preparation Examples 1 and 2 and with the data for the processes according to the invention, the following compounds of the formula (I) are obtained:

$$\underset{(I)}{Ar-X-\underset{\underset{\underset{N=\!\!=\!\!N}{\overset{|}{\underset{N}{\overset{|}{\underset{CH_2}{|}}}}}}{\overset{OH}{|}}}{C}-\underset{\overset{CH_3}{|}}{\underset{\underset{CH_3}{|}}{C}}-(CH_2)_n-N\underset{N=\!\!=\!\!\underset{R^2}{C}}{\overset{\overset{R^1}{|}\phantom{x}Y}{\underset{\phantom{x}}{\diagdown\!\!\diagup}}}}$$

| Example No. | Ar | X | n | $\underset{N=\!\!=\!\!\underset{R^2}{C}}{\overset{\overset{R^1}{|}\phantom{x}Y}{\underset{-N\phantom{x}}{\diagdown\!\!\diagup}}}$ | M.p.(°C.) or Refractive Index ($n_D^{20}$) |
|---|---|---|---|---|---|
| 3 | 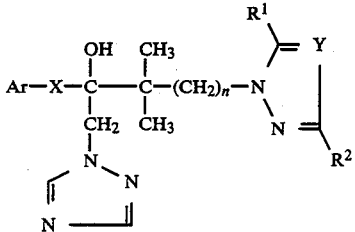 | —CH₂CH₂— | 1 | 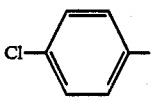 | Resin |
| 4 | 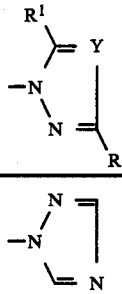 | —CH₂CH₂— | 1 | 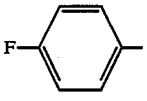 | viscous oil |
| 5 | 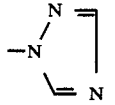 | —CH₂CH₂— | 1 |  | 96–98 |
| 6 | 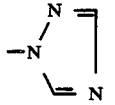 | —CH₂CH₂— | 1 | 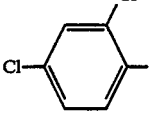 | 116–117 |
| 7 | 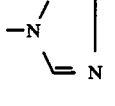 | —CH=CH— | 0 | 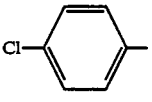 | 132 (trans-isomer) |
| 8 | 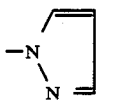 | —CH=CH— | 0 | 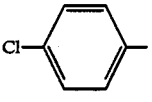 | 198 |
| 9 | 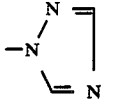 | —SCH₂— | 0 | 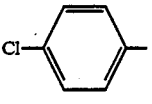 | 92 |
| 10 | 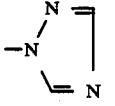 | —OCH₂— | 0 | 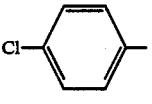 | 95 |
| 11 | 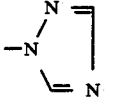 | —OCH₂— | 0 | 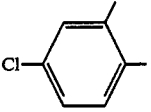 | 140 |

-continued
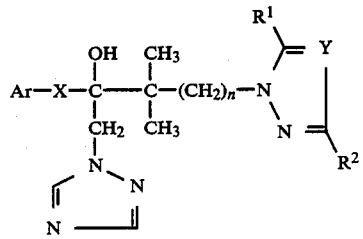  (I)
| Example No. | Ar | X | n | -N(R¹)=Y / N=R² | M.p.(°C.) or Refractive Index ($n_D^{20}$) |
|---|---|---|---|---|---|
| 12 | 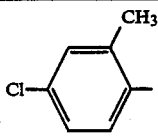 (2-CH₃, 5-Cl phenyl) | —OCH₂— | 0 | 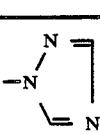 (1,2,4-triazol-1-yl) | 154 |
| 13 | 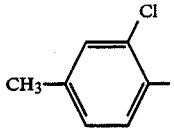 (2-Cl, 4-CH₃ phenyl) | —OCH₂— | 0 | 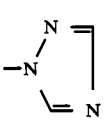 | 129 |
| 14 | 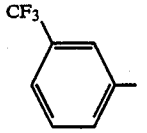 (3-CF₃ phenyl) | —OCH₂— | 0 | 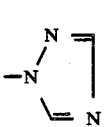 | 122 |
| 15 | 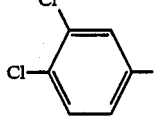 (2,3-diCl phenyl) | —OCH₂— | 0 | 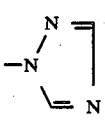 | 150 |
| 16 | 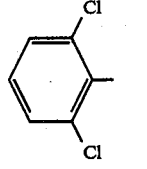 (2,6-diCl phenyl) | —CH₂CH₂— | 1 | 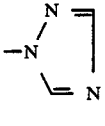 | 82–86 |
| 17 | 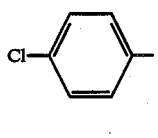 (4-Cl phenyl) | —CH₂CH₂— | 0 | 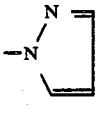 (pyrazol-1-yl) | −50 (× HCl (hygroscopic) |
| 18 | 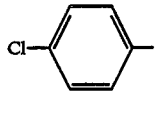 (4-Cl phenyl) | —CH₂CH₂— | 0 | 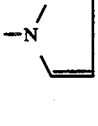 | 110 [× 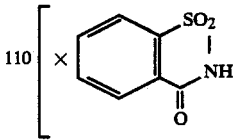 (saccharin)] |
| 19 | 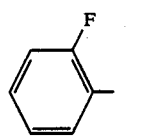 (2-F phenyl) | —CH₂CH₂— | 0 | 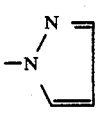 | −35 |

-continued $$Ar-X-\underset{\underset{\underset{N\phantom{=}N}{\overset{\phantom{|}}{\underset{\|}{N}}}}{\underset{|}{\underset{CH_2}{|}}}}{\overset{\overset{OH}{|}}{C}}-\underset{\underset{CH_3}{|}}{\overset{\overset{CH_3}{|}}{C}}-(CH_2)_n-\underset{\underset{R^2}{\diagdown}}{\overset{\overset{R^1}{\diagup}}{N}}\overset{Y}{\underset{\|}{N}}$$  (I)

| Example No. | Ar | X | n | $\underset{\underset{R^2}{\diagdown}}{\overset{\overset{R^1}{\diagup}}{-N}}\overset{Y}{\underset{\|}{N}}$ | M.p.(°C.) or Refractive Index ($n_D^{20}$) |
|---|---|---|---|---|---|
| 20 | 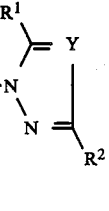 | —CH₂CH₂— | 0 | 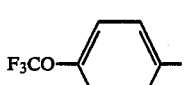 | 92 |
| 21 | 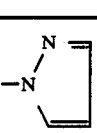 | —CH₂CH₂— | 0 | 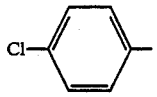 | 01 |
| 22 | 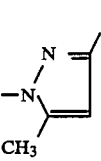 | —CH₂CH₂— | 0 | 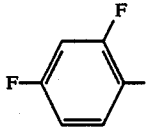 | 104 |
| 23 | 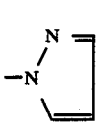 | —CH₂CH₂— | 0 | 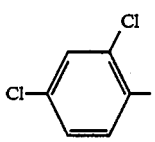 | 84 |
| 24 | 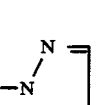 | —CH₂CH₂— | 0 | 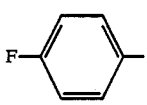 | 120 |
| 25 | 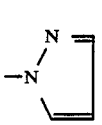 | —CH₂CH₂— | 0 | 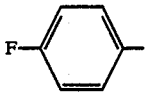 | $n_D^{20} = 1.5394$ |
| 26 | 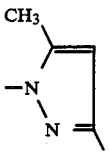 | —CH₂CH₂— | 0 | 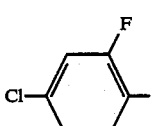 | 102 |
| 27 | 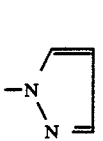 | —CH₂CH₂— | 0 | 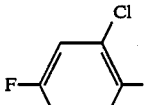 | $n_D^{20} = 1.5399$ |

-continued

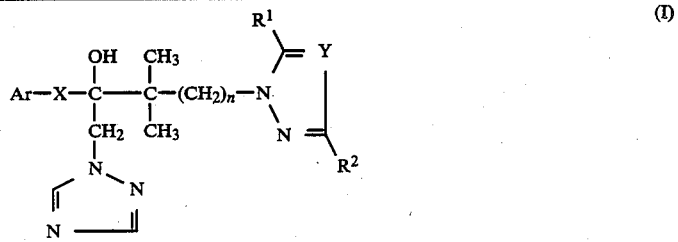

| Example No. | Ar | X | n | $\begin{array}{c}R^1\\ -N\diagdown\quad Y\\ \quad N=\!\!\!=\!\!\!\diagup\\ \quad R^2\end{array}$ | M.p.(°C.) or Refractive Index ($n_D^{20}$) |
|---|---|---|---|---|---|
| 28 |  | —OCH$_2$— | 0 |  | 146 |
| 29 |  | —CH$_2$CH$_2$— | 0 |  | viscous oil |
| 30 |  | —CH$_2$CH$_2$— | 1 |  | 109 |

In the following use examples, the compounds listed below are employed as comparison substances:

(A)

(disclosed in EP-OS (European Patent Specification) No. 0,044,605)

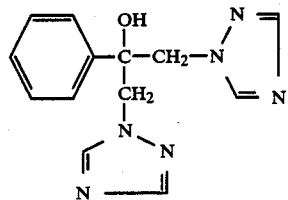

(B)

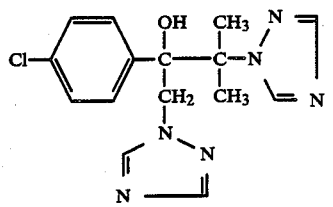

(C)

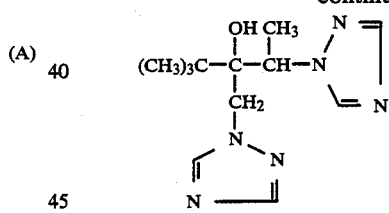

(D)

(disclosed in EP-OS (European Patent Specification) No. 0,131,845)

EXAMPLE A

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis f.sp. hordei.*

The plants are placed in a greenhouse at a temperature of about 20° C. and a relative atmospheric humidity of about 80%, in order to promote the development of powdery mildew pustules.

Evaluation is carried out 7 days after the inoculation.

In this test, the substances according to the invention which are described in Examples 2,4,7,8,10,12 and 15, show a considerably better activity than the comparison substance (B).

EXAMPLE B

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23 to 24° C. and at a relative atmospheric humidity of about 75%.

Evaluation is carried out 10 days after the inoculation.

In this test, the substance according to the invention described in Example 10 shows a considerably better activity than the comparison substances (A), (B) and (C).

EXAMPLE C

Venturia test (apple)/curative
Solvent: 0.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous conidia suspension of the apple scab causative organism (*Venturia inaequalis*). The plants remain in an incubation cabin at 20° C. and 100% relative atmospheric humidity for 1 day and are then placed in a greenhouse. After a given number of hours, the plants are sprayed with the preparation of active compound until dripping wet.

Evaluation is carried out 12 days after the inoculation.

In this test, the substances according to the invention which are described in Examples 7 and 15 show a considerably better activity than the comparison substances (C) and (D).

It will be appreciated that the instant specification and claims are set forth by way of illustration and not limitation and that various modifications and changes may be made without departing from the spirit and scope of the present invention.

What is claimed is:

1. A bisazolyl-hydroxyalkyl derivative of the formula

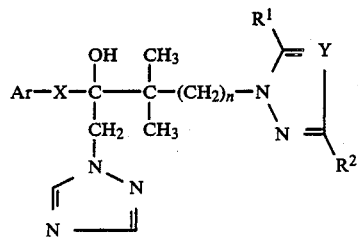

in which

Ar stands for phenyl which is optionally monosubstituted or disubstituted by identical or different substituents selected from the group consisting of fluorine, chlorine, methyl, trifluoromethyl, trifluoromethoxy and phenyl, or Ar stands for naphthyl, X represents the groupings $-CH_2-CH_2-$, $-OCH_2-$, $-SCH_2-$ or $-CH=CH-$, where the heteroatom is bonded to the phenyl radical if X stands for $-OCH_2-$ or $-SCH_2-$, Y stands for a nitrogen atom or the grouping $CR^3$, $R^1$ and $R^2$ stand for hydrogen or methyl, $R^3$ stands for hydrogen, and n stands for the numbers 0 or 1, or a hydrochloric acid or saccharin addition salt or metal salt complex thereof.

2. A compound according to claim 1 wherein such compound is 5-(4-chlorophenyl)-2-methyl-2-(pyrazol-1-yl)-3-(1,2,4-triazol-methyl)-pent-4-en-3-ol of the formula

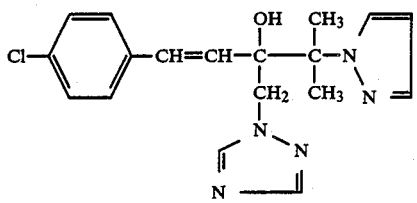

or an acid addition salt or metal salt complex thereof.

3. A compound according to claim 1 wherein such compound is 4-(4-chlorophenoxy)-2-methyl-2-(1,2,4-triazolyl)-3-(1,2,4-triazol-methyl)-butan-3-ol of the formula

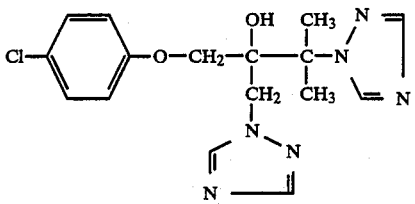

or an acid addition salt or metal salt complex thereof.

4. A compound according to claim 1 wherein such compound is 4-(3,4-dichlorophenoxy)-2-methyl-2-(1,2,4-triazolyl) -3-(1,2,4-triazol-methyl)-butan-3-ol of the formula

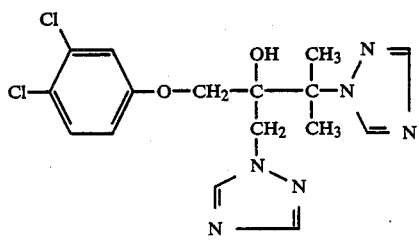

or an acid addition salt or metal salt complex thereof.

5. A compound according to claim 1 wherein such compound is 5-(2,4-difluorophenyl)-2-methyl-2-pyrazol-1-yl) -3-(1,2,4-triazol-methyl)-pentan-3-ol of the formula

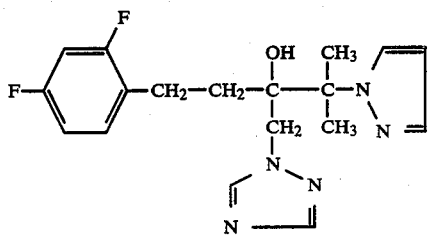

or an acid addition salt or metal salt complex thereof.

6. A compound according to claim 1 wherein such compound is 5-(4-chlorophenyl)-2-methyl-2-(1,2,4-triazolyl)-3-(1,2,4-triazol-methyl)-pentan-3-ol of the formula

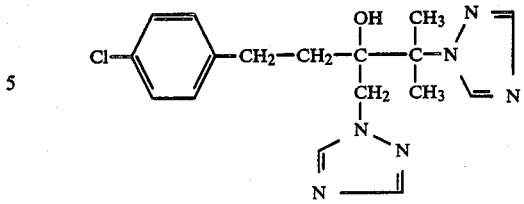

or an acid addition salt or metal salt complex thereof.

7. A fungicidal composition comprising a fungicidally effective amount of a compound, salt or complex according to claim 1 and an inert diluent.

8. A method of combating fungi which comprises applying to such fungi or to a fungus habitat a fungicidally effective amount of a compound, salt or complex according to claim 1.

9. The method according to claim 8, wherein such compound is
5-(4-chlorophenyl)-2-methyl-2-(pyrazol-1-yl)-3-(1,2,4-triazol-methyl)-pent-4-en-3-ol,
4-(4-chlorophenoxy)-2-methyl-2-(1,2,4-triazolyl) -3-(1,2,4-triazol-methyl)-butan-3-ol,
4-(3,4-dichlorophenoxy)-2-methyl-2-(1,2,4-triazolyl) -3-(1,2,4-triazol-methyl)-butan-3-ol, 4-(3,4-dichlorophenoxy)-2-methyl-2-(1,2,4-triazolyl) -3-(1,2,4-triazol-methyl)-butan-3-ol, 5-(2,4-difluorophenyl)-2-methyl-2-(pyrazol-1-yl) -3-(1,2,4-triazol-methyl)-pentan-3-ol, or 5-(4-chlorophenyl)-2-methyl-2-(1,2,4-triazolyl)-3-(1,2,4-triazol-methyl)-pentan-3-ol, or an acid addition salt or metal salt complex thereof.

* * * * *

UNITED STATES PATENT AND TRADEMARK OFFICE
CERTIFICATE OF CORRECTION

PATENT NO. : 4,960,781

DATED : October 2, 1990

INVENTOR(S) : Holmwood et al.

It is certified that error appears in the above-identified patent and that said Letters Patent is hereby corrected as shown below:

Title Page      FOREIGN PATENT DOCUMENTS: After " 0180838 " delete " 10/1986 " and substitute -- 5/1986 --

Title Page      ABSTRACT: Line 7 delete " -SH " and substitute -- -CH --

Signed and Sealed this

Fourteenth Day of July, 1992

Attest:

DOUGLAS B. COMER

*Attesting Officer*      *Acting Commissioner of Patents and Trademarks*